United States Patent
Iwasaki et al.

[11] Patent Number: 5,208,348
[45] Date of Patent: May 4, 1993

[54] MERCAPTAN COMPOUND

[75] Inventors: Tameo Iwasaki, Nishinomiya; Kazuhiko Kondo, Osaka; Hiroshi Horikawa, Kawanishi; Totaro Yamaguchi, Urawa; Tadahiro Matsushita, Hatsudo, all of Japan

[73] Assignee: Tanabe Seiyaku Co., Ltd., Osaka, Japan

[21] Appl. No.: 913,506

[22] Filed: Jul. 14, 1992

Related U.S. Application Data

[62] Division of Ser. No. 755,884, Sep. 6, 1991, Pat. No. 5,153,187.

[30] Foreign Application Priority Data

Sep. 7, 1990 [JP] Japan ................................ 3-238420
Jan. 14, 1991 [JP] Japan ................................ 2-70285

[51] Int. Cl.$^5$ .................. C07D 207/12; C07D 307/40
[52] U.S. Cl. ...................................... 548/544; 548/545
[58] Field of Search ............................... 548/544, 545

[56] References Cited

U.S. PATENT DOCUMENTS 4,138,400  2/1979  Mitzlaff ............................... 548/545
4,855,444  8/1989  Wambach ........................... 548/545

FOREIGN PATENT DOCUMENTS 0160391  11/1985  European Pat. Off. .
0280771   7/1988  European Pat. Off. .
0337637  10/1989  European Pat. Off. .

OTHER PUBLICATIONS

CA 107(3):23210k.

Primary Examiner—Marianne M. Cintins
Assistant Examiner—Rebecca Cook
Attorney, Agent, or Firm—Browdy and Neimark

[57] ABSTRACT

A mercaptan compound of the formula

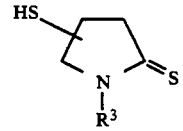

wherein $R^3$ is a hydrogen atom or a lower alkyl group, or a salt thereof.

5 Claims, No Drawings

MERCAPTAN COMPOUND

This is a division of application Ser. No. 07/755,884, filed on Sep. 6, 1991 now U.S. Pat. No. 5,153,187.

This invention relates to 1-methylcarbapenem derivatives having excellent antimicrobial activities and process for preparation thereof.

PRIOR ART

It is known that thienamycin, one of the carbapenem derivatives, has excellent antimicrobial activities against wide range of pathogenic microorganisms including Gram positive bacteria and Gram negative bacteria. Because of it's high activity against cephem-resistant bacteria, great attention is given thereto. However, thienamycin is easily deactivated by dehydropeptidase I present in the human body and is shows no activity via oral administration. From this view point, many researchers have extensively studied on new carbapenem derivatives which have excellent antimicrobial activities against various microorganisms via oral administration and are stable to dehydropeptidate I. For example, there are disclosed in Japanese Patent First Publication (Kokai) No. 49783/1990 6-(1-hydroxyethyl)-1-methyl-carbapen-2-em-3-carboxylic acids which are substituted by 2-oxo-pyrrolidin-4-ylthio group at 2-position thereof. However, there has never been known any compound having a 2-thioxo-pyrrolidin-4-yl group at 2-position of 1-methylcarbapenem nucleus.

BRIEF DESCRIPTION OF THE INVENTION

The present inventors have intensively studied on new 1-methylcarbapenem derivatives and have found that the 1-methylcarbapenem derivatives bearing 2-thioxopyrrolidin-4-yl group at 2-position of the carbapenem nucleus have superior antimicrobial activities to the known carbapenem derivatives and have superior stability against dehydropeptidase I with high absorbability by oral administration.

An object of the invention is to provide novel 1-methylcarbapenem derivatives having excellent antimicrobial activities, excellent stability against dehydropeptidase I and high absorbability by oral administration. Another object of the invention is to provide a process for preparing the novel 1-methylcarbapenem derivatives. These and other objects and advantages of the invention will be apparent to those skilled in the art from the following description.

DETAILED DESCRIPTION OF THE INVENTION

The 1-methylcarbapenem derivatives of the invention have the following formula:

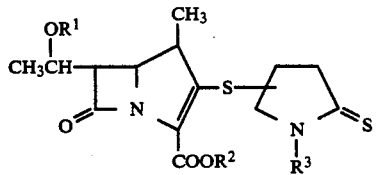

[I]

wherein $R^1$ is hydrogen atom or a hydroxy-protecting group, $R^2$ is hydrogen atom or an ester residue, $R^3$ is hydrogen atom or a lower alkyl group.

Among the compounds [I] of the invention, the compounds of the formula [I] wherein $R^1$ is hydrogen atom and $R^2$ is hydrogen atom or an ester residue which is hydrolyzed by metabolism in the human body, or salts thereof have excellent antimicrobial activities and are useful as a medicament. Besides, the compounds of the formula [I] wherein $R^2$ is a protecting group and/or $R^2$ is an ester residue which may be a carboxyl-protecting group are useful as an intermediate for preparing the above compounds having excellent antimicrobial activities.

The hydroxy-protecting group for $R^1$ in the compounds [I] includes, for example, a lower alkoxycarbonyl group, a halogeno-lower alkoxycarbonyl group, a substituted or unsubstituted phenyl-lower alkyl group (e.g. a benzyl having optionally a substituent selected from nitro and a lower alkoxy group), a tri(lower alkyl)-silyl group, a substituted or unsubstituted phenyl-lower alkoxycarbonyl group (e.g. a benzyloxycarbonyl having optionally a substituent selected from nitro and a lower alkoxy group), and the like.

The ester residue for $R^2$ includes an ester residue which can be hydrolyzed by metabolism in the human body and an ester residue which may be a carboxyl-protecting group. The ester residue hydrolyzable by metabolism in the human body includes, for example, groups of the formulae: $—A—OCOR^4$, $—A—O-COOR^4$ or $—A—O—R^4$ wherein A is a lower alkylene group, $R^4$ is a lower alkyl group, a cycloalkyl group, a lower alkenoyl group, a lower alkoxy-lower alkyl group, or a lower alkanoyloxy-lower alkyl group. Suitable examples of these ester residue are a lower alkanoyloxy-lower alkyl group, a cycloalkylcarbonyloxy-lower alkyl group, a lower alkenoyloxy-lower alkyl group, a lower alkoxy-lower alkanoyloxy-lower alkyl group, a lower alkanoyloxy-lower alkoxy-lower alkyl group, a lower alkoxy-lower alkyl group, a lower alkoxy-lower alkoxy-lower alkyl group, a lower alkoxycarbonyloxy-lower alkyl group, a lower alkoxy-lower alkoxycarbonyloxy-lower alkyl group, and the like.

The ester residue which may be a carboxyl-protecting group includes, for example, a lower alkyl group, a lower alkenyl group, a halogeno-lower alkyl group, a nitrobenzyl group, and a lower alkoxybenzhydryl group.

Through the specification and claims, the lower alkyl, lower alkylene and lower alkoxy groups have preferably 1 to 6 carbon atoms, more preferably 1 to 4 carbon atoms, and the lower alkanoyl and lower alkenyl groups have preferably 2 to 8 carbon atoms, more preferably 2 to 6 carbon atoms, and the lower alkenoyl and cycloalkyl groups have preferably 3 to 8 carbon atoms, more preferably 3 to 6 carbon atoms.

The compounds [I] of this invention can be used as a medicament either in the free form or in the form of a pharmaceutically acceptable salt thereof. The pharmaceutically acceptable salt includes, for example, non-toxic metal salts such as sodium salt, potassium salt, calcium salt, magnesium salt, aluminum salt, and the like; salts with non-toxic amines such as trialkylamines (e.g. triethylamine, etc.), pyridine, ethanolamine, triethanolamine, dicyclohexylamine, and the like; addition salts with basic amino acids such as lysine, arginine, and the like. The salt of the compounds [I] may also be a salt with a resin such as a polystyrene resin having an amino or quaternary amino group.

The compounds [I] or pharmaceutically acceptable salts thereof can be administered by oral route or parenteral route (e.g. intravenous, intramuscular or subcutaneous route). The daily dose of these compounds is in the range of about 0.002 to 0.04 g/kg of body weight, preferably about 0.005 to 0.01 g/kg of body weight. They can be used in the form of a pharmaceutical preparation suitable for oral or parenteral administration in admixture with a pharmaceutically acceptable carrier or diluent, for example, solid preparations (e.g. tablets, granules, capsules, etc.), and liquid preparations (e.g. solutions, suspensions, emulsions, etc.).

The compounds [I] include various isomers owing to the asymmetric carbon and this invention includes also these isomers and a mixture thereof. In case of using as a medicament, however, the compounds [I] have preferably R, S and S configuration at 1-, 5- and 6-position of the carbapenem nucleus, respectively, and R configuration at 1-position of the 6-substituent and further S or R configuration at the position of substitution in the pyrrolidine ring. The compounds [I] of this invention can be prepared by reacting a reactive derivative at 2-position of a ketone compound of the formula [II]:

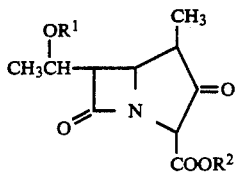

wherein $R^1$ and $R^2$ are as defined above, with a mercaptan compound of the formula [III]:

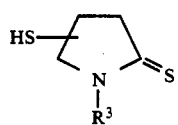

wherein $R^3$ is as defined above, or a salt thereof.

The reactive derivative at 2-position of the ketone compound [II] includes any conventional compound, for example, a compound of the formula [II-a]:

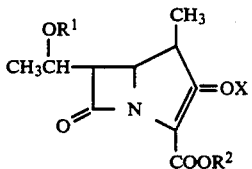

wherein $R^1$ and $R^2$ are as defined above, and X is a diphenylphosphoryl group, a di(lower alkyl)-substituted phenylphosphoryl group, a di(lower alkyl)-phosphoryl group, a lower alkanesulfonyl group, a phenylsulfonyl group, or a lower alkyl-substituted phenylsulfonyl group, which can be prepared by reacting the ketone compound [II] with the corresponding phosphoryl halide or sulfonic acid compound in the presence or absence of a base (e.g. a tri(lower alkyl)-amine, a 4-di(lower alkyl)aminopyridine, etc.).

The salt of the mercaptan compound [III] includes, for example, an alkali metal salt, a tri(lower alkyl)-ammonium salt, and the like.

The reaction of the reactive derivative of the ketone compound [II] and the mercaptan compound [III] or a salt thereof is carried out in the presence or absence of a base. The base includes any conventional base, preferably a tri(lower alkyl)amine, a 4-di(lower alkyl-)aminopyridine, and the like. The reaction is usually carried out in an appropriate solvent or without solvent under cooling (e.g. $-5°$ C. to $0°$ C.). The solvent includes any conventional inert solvent, for example, anhydrous acetonitrile, tetrahydrofuran, methylene chloride, and the like.

The compounds [I] thus prepared wherein $R^1$ is a hydroxy-protecting group and/or $R^2$ is an ester residue which may be a carboxyl-protecting group may be subjected to removal of the protecting group and/or the ester residue to give the compounds of the formula [I-a]:

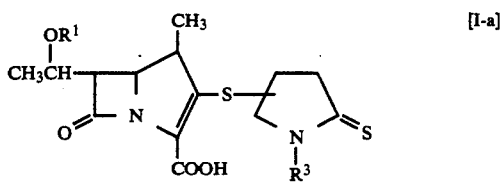

wherein $R^1$ and $R^2$ are as defined above, or a salt thereof. Removal of the protecting group or ester residue can be carried out in a usual manner.

The compounds [I-a] thus prepared may be esterified by a conventional method to give compounds of the formula [I-b]:

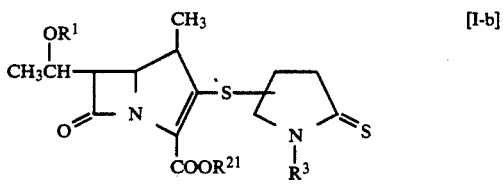

wherein $R^1$ and $R^3$ are as defined above, and $R^{21}$ is an ester residue.

Among the starting compounds, the ketone compound [II] can be prepared in the same manner as described in HETEROCYCLES, Vol. 21, page 29, 1984, and the mercaptan compound [III] can be prepared by reacting an N-substituted or unsubstituted hydroxy-2-pyrrolidone with thioacetic acid in the presence of triphenylphosphine and diethyl azodicarboxylate, followed by treating with Lawesson's reagent [=2,4-bis(4-methoxyphenyl)-1,3-dithia-2,4-diphosphetane-2,4-disulfide] and further followed by deacetylation.

The compounds of this invention are illustrated by the following Examples and Reference Examples, but should not be construed to be limited thereto.

EXAMPLES 1

(1) (1R, 5R, 6S)-6-[(1R)-1-Hydroxyethyl]-1-methyl-2-oxocarbapenam-3-carboxyl ic acid 4-nitrobenzyl ester (7.6 g) is dissolved in anhydrous acetonitrile (53 ml), and thereto are added dropwise diisopropylethylamine (2.9 g) and diphenylphosphoryl chloride (6.1 g) in this order under nitrogen gas below $0°$ C. After stirring the mixture at the same temperature for 30 minutes, a solution of (4S)-4-mercaptopyrrolidine-2-thione (2.5 g) and diisopropylethylamine (2.9 g) in anhydrous acetonitrile (53 ml) is added dropwise to the reaction mixture [which contains (1R, 5R, 6S)-6-[(1R)-1-hydroxyethyl]-1-methyl-2-diphenylphosphoryl-oxycarbapen-2-em-3-carboxylic acid 4-mitrobenzyl ester] below $-15°$ C. The mixture is stirred at the same temperature for 1.5 hour, and water (53 ml) is added to the reaction mixture, and the mixture is concentrated under reduced pressure to remove acetonitrile. The residue is extracted with ethyl acetate, and the extract is washed with brine, dried and evaporated under reduced pressure. The residue is purified by silica gel column chromatography (eluent, chloroform : ethanol =20:1) to give (1R, 5S, 6S)-2-[(4S)-pyrrolidine-2-thion-4-ylthi methylcarbapen-2-em-3-carboxylic acid 4-nitrobenzyl ester (4.7 g) as an amorphous powder.

MNR (CDCl$_3$) δppm: 1.29 (3H, d), 1.36 (3H, d), 2.90 (1H, dd), 3.23-3.34 (2H, m), 3.61-3.71 (2H, m), 4.00-4.32 (5H, m), 5.23, 5.49 (2H, d), 7.65, 8.23 (4H, d), 7.83 (1H, br.s)

(2) A mixture of the product obtained above (0.5 g), potassium hydrogen carbonate (0.105 g), tetrahydrofuran (10 ml), ethanol (10 ml) and 10% palladium-carbon (1 g) is hydrogenated at room temperature under atmospheric pressure for one hour. After removing the catalyst by filtration, the organic solvent is evaporated under reduced pressure. The aqueous layer is washed with ethyl acetate and evaporated to dryness under reduced pressure. The residue is purified with a column packed with a nonionic adsorbing resin (CHP-20P manufactured by Mitsubishi Kasei Corporation) (eluent, water) to give (1R, 5S, 6S)-2-[(4S)-pyrrolidine-2-thion-4-ylthio]-6[(1R)-1-hydroxyethl]-1-methylcarbapen-2-em-3-carboxylic acid potassium salt (0.11 g) as an amorphous powder.

MNR (D$_2$O) δppm: 1.20 (3H, d), 1.28 (3H, d), 2.84 (1H, dd), 3.24-3.47 (3H, m), 3.62-3.72 (1H, m), 4.08-4.27 (4H, m)

EXAMPLE 2

(1) In the same manner as described in Example 1-(1) except that (4R)-4-mercaptopyrrolidine-2-thione (1.1 g) is used instead of (4S)-4-mercaptopyrrolidine-2-thione, there is obtained [1R, 5S, 6S)-2-[(4R)-pyrrolidine-2-thion-4-ylthio]-6-[(1    R)-1-hydroxyethyl]-1-methlcarbapen-2-em-3-carboxylic acid 4-mitrobenzyl ester (1.8 g) as colorless needles.

M.p. 168-170° C.

MNR (DMSO) δ ppm: 1.15 (6H, d), 2.74 (1H, dd), 3.30-3.51 (4H, m), 3.97-4.31 (4H, m), 5.08 (1H, d), 5.29, 5.47 (2H, d), 7.70, 8.24 (4H, d), 10.39 (lH, br.s)

(2) The product obtained above (0.5 g) is treated in the same manner as described in Example 1-(2) to give (1R, 5S, 6S)-2-[(4R)-pyrrolidine-2-thion-4-ylthio]-6-[(1R)-1-hydroxyethyl]-1-methylcarbapen-2-em-3-carboxylic acid potassium salt (0.12 g) as an amorphous powder.

MNR (D$_2$O) δppm: 1.20 (3H, d), 1.29 (3H, d), 2.94 (1H, dd), 3.28-3.67 (4H, m), 4.06-4.27 (4H, m)

EXAMPLE 3

To a mixture of (1R, 5S, 6S)-2-[(4R)-pyrrolidine-2-thion-4-ylthio]-6-[(1R)-1R)-1-hydoxyethl]-1-methylcarapen-2-em-3-carboxylic acid potassium salt (0.34 g), N,N-dimethylformamide (3 ml) and potassium carbonate (0.12 g) is added dropwise isobutyryloxymethyl iodide (0.27 g) under ice cooling. After stirring the mixture at the same temperature for 30 minutes, ethyl acetate (10 ml) is added to the reaction mixture, and the mixture is washed with water, and the organic layer is dried and evaporated under reduced pressure to remove the solvent. The residue is purified by silica gel flash column chromatography (eluent, chloroform : ethanol =20:1), followed by crystallization from isopropyl ether and ethyl acetate to give (1R, 5S, 6S)-2-[(4R)-pyrrolidine-2-thion-4-ylthio]-6  -[(1R)-1-hydroxyethl]-1-methylcarbapen-2-em-3-carboxylic acid isobutyryloxymethyl ester (0.12 g) as colorless needles.

M.p. 158-159° C.

EXAMPLES 4 to 8

In the same manner as described in Example 3 (1R, 5S, 6S)-2-[(4R)-pyrrolidine-2-thion-4-ylthio]-6-[(1R)-1-hydroxyethyl]-1-methylcarbapen-2-em-3-carboxylic acid potassium salt is treated with various alkanoyloxmethyl iodide to prepare various ester compounds as shown in the following Table 1.

TABLE 1

| Ex. No. | R | Physical properties, etc. |
| --- | --- | --- |
| 4 | —CH$_2$OCOCH$_2$CH$_2$CH$_3$ | m.p. 115-117° C. |
| 5 | —CH$_2$OCOCH$_2$CH$_2$CH$_2$CH$_3$ | m.p. 75—77° C. |
| 6 | —CH$_2$OCOC(CH$_3$)$_3$ | m.p. 140-142° C. |
| 7 | —CH$_2$OCOCH$_2$CH$_3$ | amorphous powder MNR (CDCl$_3$) δppm: 1.16 (3H, t), 1.28 (3H, d), 1.35 (3H, d), 1.68 (1H, s), 2.41 (2H, q), 2.97 (1H, dd), 3.23-3.44 (3H, m), 3.60-3.64 (1H, m), 4.01-4.13 (2H, m), 4.21-4.30 (2H, m), 5.85, 5.94 (2H, d), 7.79 (1H, s) |
| 8 | —CH$_2$OCOCH$_2$CH(CH$_3$)$_2$ | m.p. 122-125° C. |

EXAMPLES 9 to 28

In the same manner as described in Example 3, (1R, 5S, 6S)-2-[(4S)-pyrrolidine-2-thion-4-]-6-[(1R)-1-hydroxyethyl]-1-methylcarbapen-2-em-3-carboxylic acid potassium salt is treated with various substituted methyl iodide or 1-substituted ethyl iodide to prepare various ester compounds as shown in the following Table 2.

TABLE 2

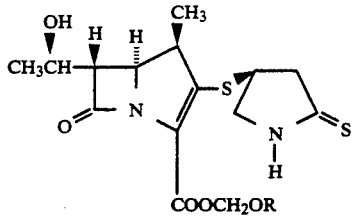

| Ex. No. | R | Physical properties, etc. |
|---|---|---|
| 9 | —COCH$_2$CH$_3$ | amorphous powder<br>MNR (CDCl$_3$) δppm: 1.16 (3H, t), 1.28 (3H, d), 1.34 (3H, d), 2.14 (1H, s), 2.41 (2H, q), 2.90 (1H, dd), 3.23-3.43 (3H, m), 3.59-3.68 (1H, m), 4.00-4.11 (2H, d), 4.22-4.30 (2H, m), 5.84, 5.94 (2H, d), 7.90 (1H, s) |
| 10 | —COCH(CH$_3$)$_2$ | m.p. 143-144° C. (decomp.) |
| 11 | —COC(CH$_3$)$_3$ | m.p. 152-153° C. (decomp.) |
| 12 | —COCH(CH$_3$)CH$_2$CH$_3$ | amorphous powder<br>MNR (CDCl$_3$) δppm: 0.90 (3H, t), 1.14 (3H, t), 1.27 (3H, d), 1.32 (3H, d), 1.40-1.85 (2H, m), 2.35-2.55 (1H, m), 2.80-3.00 (1H, m), 3.20-3.35 (2H, m), 3.20-3.40 (1H, m), 3.50-3.75 (1H, m), 4.00-4.20 (2H, m), 4.20-4.35 (2H, m), 5.80-5.95 (2H, m) |
| 13 | —CO—◁ | MNR (CDCl$_3$) δppm: 0.85-1.05 (2H, m), 1.05-1.15 (2H, m), 1.27 (3H, d), 1.34 (3H, d), 1.60-1.80 (1H, m), 2.80-3.00 (1H, m), 3.20-3.35 (2H, m), 3.20-3.40 (1H, m), 3.60-3.75 (1H, m), 3.95-4.20 (2H, m), 4.20-4.35 (2H, m), 5.83, 5.92 (2H, ABq) |
| 14 | —COCH$_2$CH=CH$_2$ | amorphous powder<br>MNR (CDCl$_3$) δppm: 1.20-1.40 (6H, m), 2.80-3.10 (1H, m), 3.15-3.25 (2H, m), 3.25-3.35 (2H, m), 3.35-3.50 (1H, m), 3.60-3.70 (1H, m), 3.80-4.20 (2H, m), 4.20-4.35 (2H, m), 5.10-5.30 (2H, m), 5.75-6.05 (3H, m) |
| 15 | —COCH$_2$OCH$_3$ | MNR (CDCl$_3$) δppm: 1.25 (3H, d), 1.33 (3H, d), 2.85-3.00 (1H, m), 3.20-3.40 (2H, m), 3.30-3.50 (1H, m), 3.60-3.70 (1H, m), 3.95-4.20 (2H, m), 4.20-4.35 (2H, m), 4.10 (3H, s), 5.80-6.10 (2H, m) |
| 16 | —COCH$_2$CH(CH$_3$)$_2$ | amorphous powder<br>MNR (CDCl$_3$) δppm: 0.96 (6H, d), 1.27 (3H, d), 1.34 (3H, d), 2.00-2.20 (1H, m), 2.20-2.30 (2H, m), 2.80-3.00 (1H, m), 3.20-3.35 (2H, m), 3.35-3.55 (1H, m), 3.55-3.75 (1H, m), 3.95-4.20 (2H, m), 4.20-4.35 (2H, m), 3.85, 5.93 (2H, ABq) |
| 17 | —COCH$_3$ | amorphous powder<br>MNR (CDCl$_3$) δppm: 1.27 (3H, d), 1.33 (3H, d), 2.13 (3H, s), 2.80-3.00 (1H, m), 3.20-3.35 (2H, m), 3.30-3.45 (1H, m) |
| 18 | —COCH$_2$CH$_2$CH$_2$CH$_3$ | amorphous powder<br>MNR (CDCl$_3$) δppm: 0.91 (3H, t, J=7.2Hz), 1.28 (3H, d, J=7.3Hz), 1.33 (3H, d, J=6.2Hz), 1.54-1.70 (4H, m), 2.39 (2H, t, J=7.7Hz), 2.83-2.96 (1H, m), 3.25-3.42 (3H, m), 3.59-3.71 (1H, m), 4.03-4.10 (2H, m), 4.24-4.30 (2H, m), 5.83, 5.93 (2H, ABq, J=5.6Hz), 8.10 (1H, br) |
| 19 | —COCH$_2$CH$_2$CH$_3$ | amorphous powder<br>MNR (CDCl$_3$) δppm: 0.96 (3H, t, J=7.4Hz), 1.28 (3H, d, J=7.3Hz), 1.33 (3H, d, J=6.2Hz), 1.54-1.76 (2H, m), 2.37 (2H, t, J=7.5Hz), 2.89 (1H, dd, J=4.9, 18.4Hz), 3.25-3.52 (3H, m), 3.64-3.67 (1H, m), 4.02-4.10 (2H, m), 4.23-4.29 (2H, m), 5.83, 5.93 (2H, ABq, J=5.6Hz), 7.99 (1H, br) |
| 20 | —COCH$_2$OCH$_2$CH$_3$ | amorphous powder<br>MNR (CDCl$_3$) δppm: 1.21-1.35 (9H, m), 2.87 (1H, dd, J=5.0, 18.0Hz), 3.26– |

TABLE 2-continued

| | | |
|---|---|---|
| 21 | —CH₂CH₂OCOCH₂CH₃ | 3.41 (3H, m), 3.57-3.71 (3H, m), 4.02-4.30 (6H, m), 5.86, 6.02 (2H, ABq, J=5.6Hz), 8.11 (1H, br)<br>amorphous powder<br>MNR (CDCl₃) δppm: 1.05-1.15 (3H, m), 1.27 (3H, d), 1.33 (3H, d), 2.35 (2H, q), 2.80-3.00 (1H, m), 3.15-3.30 (2H, m), 3.25-3.40 (1H, m), 3.55-3.70 (1H, m), 3.80-4.15 (4H, m), 4.15-4.35 (4H, m), 5.30, 5.61 (2H, ABq) |
| 22 | —CH₃ | m.p. 166-168° C. |
| 23 | —CH₂CH₂OCH₃ | amorphous powder<br>MNR (CDCl₃) δppm: 1.27 (3H, d), 1.33 (3H, d), 2.80-3.00 (1H, m), 3.15-3.30 (2H, m), 3.40 (3H, s), 3.50-3.70 (4H, m), 3.80-3.95 (2H, m), 4.00-4.15 (2H, m), 4.15-4.35 (2H, m), 5.31, 5.61 (2H, ABq) |

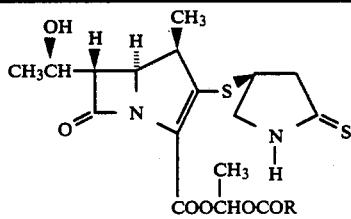

| Ex. No. | R | Physical properties, etc. |
|---|---|---|
| 24 | —CH₃ | amorphous powder<br>MNR (CDCl₃) δppm: 1.24-1.34 (6H, m), 1.54-1.58 (3H, m), 2.08, 2.11 (3H, s), 2.83-2.96 (1H, m), 3.28-3.41 (3H, m), 3.62-3.68 (1H, m), 4.06 (2H, m), 4.25 (2H, m), 6.92-7.08 (1H, m), 8.15 (1H, br) |
| 25 | —CH(CH₃)₂ | amorphous powder<br>MNR (CDCl₃) δppm: 1.14-1.36 (12H, m), 1.54-1.58 (3H, m), 2.49-2.66 (1H, m), 2.83-2.93 (1H, m), 3.25-3.42 (3H, m), 3.59-3.67 (1H, m), 4.03-4.10 (2H, m), 4.22-4.28 (2H, m), 6.91-7.01 (1H, m) 8.20 (1H, br) |
| 26 | —OCH(CH₃)₂ | amorphous powder<br>NMR (CDCl₃) δppm: 1.25-1.35 (12H, m) 1.60 (3H, t, J=4.9Hz), 2.88 (1H, dd, J=4.6, 18.2Hz), 3.25-3.42 (3H, m), 1.65 (1H, m), 4.06-4.10 (2H, m), 4.24-4.28 (2H, m), 4.83-4.98 (1H, m), 6.83-6.88 (1H, m), 8.19 (1H, br) |
| 27 | —OCH₂CH₃ | amorphous powder<br>MNR (CDCl₃) δppm: 1.22-1.37 (9H, m), 1.60 (3H, t, J=4.4Hz), 2.87 (1H, dd, J=4.7, 18.2Hz), 3.25-3.42 (3H, m), 3.62-3.66 (1H, m), 4.06-4.30 (6H, m), 6.84-6.88 (1H, m), 8.13 (1H, br) |
| 28 | —OCH₂CH₂OCH₂CH₃ | amorphous powder<br>MNR (CDCl₃) δppm: 1.17-1.35 (9H, m), 1.58-1.62 (3H, m), 2.86 (1H, dd, J=4.6, 18.3 Hz), 3.26-3.42 (3H, m), 3.49-3.71 (5H, m), 4.07-4.11 (2H, m), 4.24-4.34 (4H, m), 6.61-6.91 (1H, m), 8.13 (1H, br) |

EXAMPLE 29

(1) (1R, 5R, 6S)-6-]-(1R)-1-Hydroxyethyl]-1-methyl-2-oxocarbapenam-3-carboxyl ic acid 4-nitrobenzyl ester (25.2 g) is dissolved in anhydrous acetonitrile (173 ml), and thereto are added dropwise diisopropylethylamine (13 ml) and diphenylphosphoryl chloride (15.5 ml) in this order under nitrogen gas below 0° C. After stirring the mixture at the same temperature for 30 minutes, a solution of (4R)-N-methyl-4-mercaptopyrrolidine-2-thione (13 g) and diisopropylethylamine (11.5 g) in anhydrous acetonitrile (173 ml) is added dropwise to the reaction mixture below −5° C. After stirring the mixture at 0° C. for 1.5 hour, the reaction mixture is poured into phosphate buffer (pH 7.0, one liter). The precipitated crystal is separated by filtration and dissolved in a mixture of chloroform (2 liters) and tetrahydrofuran (1 liter), and the solution is washed with water, dried and concentrated to dryness under reduced pressure. The residue is crystallized from diethyl ether to give (1R, 5S, 6S)-2-[(4R)-N-methyl-pyrrolidine-2-thion-4-ylthio]-6-[(1R)-1-hydroxyethyl]-1-methylcarpena-2-em-3-carboxylic acid 4-nitrobenzyl ester (23.5 g) as colorless needles.

M.p. 157-158° C.

(2) A mixture of the product obtained above (6 g), tetrahydrofuran (250 ml), ethanol (250 ml), sodium hydrogen carbonate (1.03 g), water (250 ml) and 10% palladium-carbon (water content 52%, 22,8 g) is hydrogenated at room temperature under atmospheric pressure for 1.5 hour. After removing the catalyst by filtration, the organic solvent is evaporated under reduced pressure. The aqueous layer is washed with ethyl acetate, treated with activated charcoal and filtered. The filtrate is concentrated under reduced pressure, and the residue is crystallized from ethanol to give (1R, 5S, 6S)-2-[(4R)-N-methylpyrrolidine-2-thion-4-ylthio]-6-[(1R)-1-hydroxyethyl]-1-methylcarbapen-2-em-3-carboxylic acid sodium salt (3.2 g) as colorless needles.

M.p. 170–180° C. (decomp.)

EXAMPLE 30

(1R, 5S, 6S)-2-[(4R)-N-methylpyrrolidine-2-thion-4-ylthio]-6-[(1R)-1-hydro yethyl]-1-methcarbapen-2-em-3-carboxylic acid sodium salt (400 mg) is suspended in N,N-dimethylformamide (5 ml), and thereto is added potassium carbonate (146 mg). To the mixture is added acetoxymethyl iodide (275 mg) at 5–7° C., and the mixture is stirred at the same temperature for one hour. The reaction mixture is poured into phosphate buffer (pH 7.0) and extracted with ethyl acetate. The organic layer is washed with water, dried and concentrated to dryness under reduced pressure. The residue is purified by silica gel column chromatography (eluent, chloroform - chloroform : ethanol =98:2), followed by crystallization from tetrahydrofuran and diethyl ether to give (1R, 5S, 6S)-2-[(4R)-N-methylpyrrolidine-2-thion-4-ylthio]-6-[(1R)-1-hydroxye thyl]-1-methylcarbapen-2-em-3-carboxylic acid acetoxymethyl ester (250 mg) as colorless needles.

M.p. 124–126° C.

EXAMPLES 31 TO 37

In the same manner as described in Example 30, (1R, 5S, 6S)-2-[(4R)-N-methylpyrrolidine-2-thion-4-ylthio]-6-[1R)-1-hydroxyethyl]-1 -methylcarbapen-2-em-3-carboxylic acid sodium salt is treated with various substituted methyl iodides to prepare various ester compounds as shown in the following Table 3.

TABLE 3

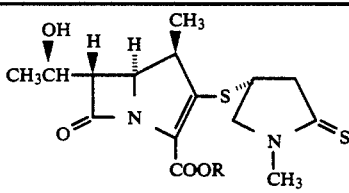

| Ex. No. | R | Physical properties, etc. |
|---|---|---|
| 31 | —CH₂OCOCH₂CH₃ | m.p. 93–97° C. |
| 32 | —CH₂OCOCH₂CH₂CH₃ | m.p. 148–149° C. |
| 33 | —CH₂OCOCH(CH₃)₂ | m.p. 138–141° C. |
| 34 | —CH₂OCO—◁ | m.p. 133–135° C. |
| 35 | —CH₂OCO(CH₂)₃CH₃ | m.p. 122–123° C. |
| 36 | —CH₂OCOCH₂CH(CH₃)₂ | m.p. 130–132° C. |
| 37 | —CH₂OCOC(CH₃)₃ | m.p. 159–160° C. |

EXAMPLE 38

(1) In the same manner as described in Example 29-(1), (1R, 5R, 6S)-6-[(1R)-1-hydroxyethyl]-1-methyl-2-oxo-carbapenam-3-carboxylic acid 4-nitrobenzyl ester is treated with (4S)-N-methyl-4-mercaptopyrrolidine-2-thione to give (1R, 5S, 6S)-2-[(4S)-N-methylpyrrolidine-2-thion-4-ylthio]--[(1R)-1-hydroxyethyl]-1-methylcarbapen-2-em-3-carboxylic acid 4-nitrobenzyl ester as an amorphous powder.

MNR (CDCl₃) δppm: 1.29 (3H, d), 1.36 (3H, d), 3.00–3.15 (1H, m), 3.25 (3H, s), 3.15–3.35 (2H, m), 3.40–3.60 (1H, m), 3.65–3.80 (1H, m), 3.85–4.00 (1H, m), 4.05–4.20 (1H, m), 4.20–4.35 (2H, m), 5.22, 5.50 (2H, ABq), 7.64, 8.23 (4H, A₂B₂q)

(2) The product obtained above is treated in the same manner as described in Example 29-(2) to give (1R, 5S, 6S)-2-[(4S)-N-methylpyrrolidine-2-thion-4-ylthio]-6-[(1R)-1-hydroxyethyl]-1-methy carbapena-2-em-3-carboxylic acid nodium salt as colorless needles.

M.p. 185–190° C. (decomp.)

EXAMPLES 39 TO 46

In the same manner as described in Example 30, (1R, 5S, 6S)-2-[(4S)-N-methylpyrrolidine-2-thion-4-ylthio]-6-[(1R)-1-hydroxyethyl]-1-methylcarbapen-2-em-3-carboxylic acid sodium salt is treated with various substituted methyl iodides to prepare various ester compounds as shown in the following Table 4.

TABLE 4

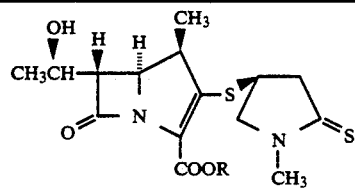

| Ex. No. | R | Physical properties, etc. |
|---|---|---|
| 39 | —CH₂OCOCH₃ | m.p. 165–167° C. |
| 40 | —CH₂OCOCH₂CH₃ | m.p. 138–139° C. |
| 41 | —CH₂OCOCH₂CH₂CH₃ | m.p. 127–128° C. |
| 42 | —CH₂OCOCH(CH₃)₂ | m.p. 163–164° C. |
| 43 | —CH₂OCO—◁ | m.p. 130–133° C. |
| 44 | —CH₂OCO(CH₂)₃CH₃ | m.p. 119–121° C. |
| 45 | —CH₂OCOCH₂CH(CH₃)₂ | m.p. 133–136° C. |
| 46 | —CH₂OCOC(CH₃)₃ | m.p. 167–169° C. |

EXAMPLE 47

(1) (1R, 5R, 6S)-6-](1R)-1-Hydroxyethyl-1-methyl-2-oxocarbapenam-3-carboxylic acid 4-nitrobenzyl ester (8.3 g) is dissolved in anhydrous acetonitrile (50 ml), and thereto are added dropwise diisopropylethylamine (4 ml) and diphenylphosphoryl chloride (4.8 ml) in this order under nitrogen gas below 0° C. After stirring the mixture at the same temperature for 30 minutes, a solution of (3R)-3-mercaptopyrrolidine-2-thione (4 g) and diisopropylethylamine (4 ml) in anhydrous acetonitrile (50 ml) is added dropwise to the reaction mixture below −15° C. The mixture is stirred at the same temperature for 1.5 hour, and water (50 ml) is added to the reaction mixture. The mixture is concentrated under reduced pressure to remove acetonitrile. The residue is extracted with ethyl acetate, and the extract is washed with water, dried and evaporated to dryness under reduced pressure. The residue is purified by silica gel column chromatography (eluent, chloroform : methanol =99:1) to give (1R, 5S, 6S)-2-[(3R)-pyrrolidine-2-thion-3-ylthio]-6-[(1R)-1-hydroxyethy l]-1-methylcarbapen-2-em-3-carboxylic acid 4-nitrobenzyl ester (4.3 g) as an amorphous powder.

MNR (CDCl₃) δppm: 1.20–1.40 (6H, m), 1.68 (1H, br.s), 2.20–2.40 (1H, m), 2.60–2.80 (1H, m), 3.30–3.50 (1H, m), 3.30–3.40 (1H, m), 3.60–3.90 (2H, m), 4.20–4.40 (2H, m), 4.40–4.50 (1H, m), 5.22 (1H, d), 5.50 (1H, d), 7.62 (2H, d), 8.12 (1H, br.s), 8.22 (2H, d)

(2) A mixture of the product obtained above (2 g), water (78 ml), tetrahydrofuran (39 ml), ethanol (39 ml), potassium hydrogen carbonate (0.42 g) and 10% palladium-carbon (4 g) is hydrogenated at room temperature under atmospheric pressure for 2 hours. After removing the catalyst by filtration, the organic solvent is evaporated under reduced pressure. The aqueous layer is washed with ethyl acetate and concentrated to dryness under reduced pressure. The residue is purified with a column packed with a nonionic adsorbing resin (CHP-20P manufactured by Mitsubishi Kasei Corporation) (eluent, water) to give (1R, 5S, 6S)-2-[(3R)-pyrrolidine-2-thion-3-ylthio]-6-[(1R)-1-hydroxyethyl]-1-met hylcarbapen-2-em-3-carboxylic acid potassium salt (0.9 g) as an amorphous powder.

NMR (D₂O) δppm: 1.20–1.40 (6H, m), 2.20–2.40 (1H, m), 2.60–2.80 (1H, m), 3.30–3.50 [2H, m), 3.70–3.90 (2H, m), 4.20–4.40 (2H, m), 4.50–4.60 (1H, m)

EXAMPLE 48

(1R, 5S, 6S)-2-[(3R)-Pyrrolidine-2-thion-3-ylthio]-6-[(1R)-1-hydroxyethyl]-1-methylcarbapen-2-em-3-carboxylic acid potassium salt (0.5 g) is suspended in N,N-dimethylformamide (5 ml). To the suspension is added isobutyryloxymethyl iodide (338 mg) under ice cooling, and the mixture is stirred at the same temperature for 30 minutes. To the reaction mixture is added ethyl acetate, and the mixture is washed with water, dried and concentrated to dryness under reduced pressure. The residue is purified by silica gel flash column chromatography (eluent, chloroform : methanol =20:1) to give (1R, 5S, 6S)-2-[(3R)-pyrrolidine-2-thion-3-ylthio]-6-[(1R)-1-methylcarbapen-2-em-3-carboxylic acid isobutyryloxymethyl ester (0.14 g) as an amorphous powder.

MNR (CDCl₃) 4ppm: 1.20–1.40 (12H, m), 2.20–2.40 (2H, m), 2.60–2.90 (2H, m), 3.30–3.40 (2H, m), 3.60–3.90 (2H, m), 4.20–4.30 (2H, m), 4.40–4.50 (1H, dd), 5.87 (1H, d), 5.98 (1H, d), 8.15 (1H, br.s)

EXAMPLE 49

In the same manner as described in Example 47, (1R, 5R, 6S)-6-[(1R)-1-hydroxyethyl]-1-methyl-2-oxocarbapenam-3-carboxylic acid 4-nitrobenzyl ester is treated with (3S)-3-mercaptopyrrolidine-2-thione to give (1R, 5S, 6S)-2-[(3S)-pyrrolidine-2-thion-3-ylthio]-6-[(1R)-1-hydroxye yl]-1-methycarbapen-2-em-3-carboxylic acid potassium salt.

NMR (D₂O) δppm: 1.20–1.40 (6H, m), 2.20–2.40 (1H, m), 2.70–2.90 (1H, m), 3.40–3.50 (1H, m), 3.60–3.90 (3H, m), 4.20–4.40 (3H, m)

EXAMPLE 50

In the same manner as described in Example 48, (1R, 5S, 6S)-2-[(3S)-pyrrolidine-2-thion-3-ylthio]-6-[(1R)-1-hydroxyethyl]-1-met hylcarbapen-2em-3-carboxylic acid potassium salt is treated with isobutyryloxymethyl iodide to give (1R, 5S, 6S)-2-[(3S)-pyrrolidine-2-thion-3-ylthio]-6-[(1R)-1-hydroxyethy l]-1-methylcarbapen-2-em-3-carboxylic acid isobutyryloxymethyl ester. hydroxyethyl]-1-methylcarbapen-2-em-3-carboxylic acid MNR (CDCl₃) δppm: 1.10–1.40 (12H, m), 2.10–2.40 (2H, m), 2.50–2.80 (2H, m), 3.20–3.30 (1H, m), 3.60–3.90 (3H, m), 4.20–4.40 (3H, m), 5.84 (1H, d), 5.94 (1H, d), 7.82 (1H, br.s)

REFERENCE EXAMPLE 1

(1) (4R)-4-Hydroxy-2-pyrrolidone (4.5 g) is suspended in tetrahydrofuran (300 ml), and thereto is added triphenylphosphine (23.4 g). After stirring the mixture for 10 minutes, diethyl azodicarboxylate (14 ml) is added dropwise to the mixture below −10° C., and the mixture is stirred at the same temperature for 10 minutes. Thioacetic acid (6.3 ml) is added dropwise to the reaction mixture below −10° C., and the mixture is stirred at the same temperature for 2 hours, and the solvent is evaporated under reduced pressure. The residue is crystallized from diisopropyl ether, and the precipitate is removed by filtration. The filtrate is concentrated under reduced pressure, and the residue is purified by silica gel column chromatography (eluent, chloroform : ethanol =98:2) to give (4S)-4-acetylthio-2-pyrrolidone (3.8 g) as an oil.

NMR (CDCl₃) δppm: 2.29 (1H, dd), 2.35 (3H, s), 2.81 (1H, dd), 3.31 (1H, dd), 3.88 (1H, dd), 4.10–4.23 (1H, m), 7.02–7.17 (1H, b)

(2) A mixture of the product obtained above (4.8 g), toluene (100 ml) and Lawesson's reagent [=2,4-bis(4-methoxyphenyl)-1,3-dithia-2,4-diphosphetane-2,4-disulfide](6.1 g) is refluxed for 15 minutes, and thereafter the solvent is evaporated to dryness under reduced pressure. The residue is purified by silica gel column chromatography (eluent, chloroform : ethyl acetate =95:5) to give (4S)-4-acetylthiopyrrolidine-2-thione (3.6 g) as colorless needles.

M.p. 91–92° C.

[60 $_D^{23}$ −57.5°(c =1, methanol)

(3) A mixture of the product obtained above (3.6 g) and 16 % ammonia-methanol solution (36 ml) is stirred under ice cooling for 30 minutes. After evaporation of the solvent, the residue is coevaporated with toluene (36 ml) to give (4S)-4-mercaptopyrrolidine-2-thione (2.7 g). The crude product thus obtained is used in the subsequent step without further purification.

Reference Example 2

(1) (4S)-4-Hydroxy-2-pyrrolidone (1.7 g) is treated in the same manner as described in Reference Example 1-(1) to give (4R)-4-acetylthio-2-pyrrolidone (2 g) as an oil.

NMR (CDCl₃) δppm: 2.29 (1H, dd), 2.35 (3H, s), 2.80 (1H, dd), 3.31 (1H, dd), 3.89 (1H, dd), 4.10–4.23 (1H, m)

(2) The product obtained above (1.9 g) is treated in the same manner as described in Reference Example 1-(2) to give (4R)-4-acetylthiopyrrolidine-2-thione (1.8 g) as colorless needles.

M.p. 91–93° C.

[α]$_D^{25}$ +57.7°(c =1, methanol)

(3) The product obtained above (1.7 g) is treated in the same manner as described in Reference Example 1-(3) to give (4R)-4-mercaptopyrrolidine-2-thione (1.3 g). The crude product thus obtained is used in the subsequent step without further purification.

Reference Example 3

(1) A mixture of (4S)-N-benzyloxycarbonyl-4-hydroxy-2-pyrrolidone (116 g), t-butyldimethylsilyl chloride (81.4 g), imidazole (67.4 g) and dimethylformamide (350 ml) is stirred at room temperature for 17 hours, and the solvent is evaporated in vacuo. To the residue is added ethyl acetate, and the mixture is washed with water, dried and concentrated under reduced pressure. The residue is purified by silica gel column chromatography (eluent, n-hexane : ethyl acetate =4:1 to 2:1) to give (4S)-N-benzyloxycarbonyl-4-t-butyldimethylsilyloxy-2-pyrrolidone (160 g) as colorless needles.

M.p. 59–60° C.

(2) The product obtained above (160 g) is dissolved in methanol (1 liter) and thereto is added palladium black (5 g). The mixture is subjected to catalytic hydrogenation (hydrogen pressure 3.5 kg/cm$^2$, at room temperature, for one hour). After filtering off the catalyst, the filtrate is concentrated under reduced pressure, and the residue is purified by silica gel column chromatography (eluent, n-hexane : ethyl acetate =2:1 to 1:2) to give (4S)-4-t-butyldimethylsilyloxy-2-pyrrolidone (51 g) as colorless needles.

M.p. 90–93° C.

(3) The product obtained above (51 g) is added to a suspension of sodium hydride (62%, 10.1 g) in dimethylformamide (510 ml) at −40° C., and after 10 minutes, iodide (37 g) is added thereto. The mixture is heated with stirring to 40° C. over a period of 1.5 hour, and thereto is added acetic acid. The reaction mixture is poured into ice water (1.5 liter) and extracted with ethyl acetate. The organic layer is washed with water, dried and concentrated under reduced pressure. The residue is purified by silica gel column chromatography to give (4S)-N-methyl-4-t-butyl-dimethylsilyloxy-2-pyrrolidone (41 g) as a colorless oil.

NMR (CDCl$_3$δppm: 0.00 (6H, s), 0.81 (9H, s), 2.20–2.32 (1H, m), 2.45–2.60 (1H, m), 2.78,(3H, s), 3.12–3.20 (1H, m), 3.45–3.50 (1H, m), 4.30–4.42 (1H, m)

(4) The product obtained above (41 g) is dissolved in methanol (250 ml), and thereto is added 6N hydrochloric acid (40 ml) under ice cooling. The mixture is stirred at room temperatue for 10 minutes. After completion of the reaction, the reaction mixture is neutralized with sodium hydrogen carbonate (30 g), and evaporated under reduced pressure. The residue is washed with ethyl acetate and evaporated to dryness under reduced pressure. Acetone is added to the residue and undissolved substance is removed by filtration. The filtrate is concentrated under reduced pressure, and the residue is purified by silica gel column chromatography (eluent, chloroform : ethanol =10:1) to give (4S)-N-methyl-4-hydroxy-2-pyrrolidone (21 g) as a colorless oil.

NMR (CDCl$_3$) δppm: 2.30–2.40 (1H, m), 2.60–2.75 (1H, m), 2.65 (3H, s), 3.25–3.35 (1H, m), 3.60–3.70 (1H, m), 4.40–4.50 (1H, m), 4.64 (1H, d)

(5) The product obtained above (21.3 g) is treated in the same manner as described in Reference Example 1-(1) and -(2) to give (4R)-N-methyl-4-acetylthiopyrrolidine-2-thione (26 g) as an yellow oil.

NMR (CDCl$_3$) 4ppm: 2.35 ,(3H, s), 2.90–3.05 (1H, m), 3.26 (3H, s), 3.40–3.55 (1H, m), 3.60–3.70 (1H, m), 4.05–4.15 (1H, m), 4.15–4.30 (1H, m)

(6) A mixture of the product obtained above (16.9 g) and 16% ammonia-methanol solution (100 ml) is stirred at room temperature for 20 minutes. After evaporation of the solvent under reduced pressure, acetonitrile (50 ml) is added to the residue, and the mixture is concentrated to give (4R)-N-methyl-4-mercaptopyrrolidine-2-thione (13 g). The crude product thus obtained is used in the subsequent step without further purification.

Reference Example 4

(1) (3R)-3-Acetylthiopyrrolidin-2-one (9 g) is treated in the same manner as described in Reference Example 1-(2) to give (3R)-3-acetylthiopyrrolidine-2-thione (6.4 g).

M.p. 98–100° C.

$[\alpha]_D^{23}$ −123.1°(c =0.72, methanol)

(2) A mixture of the product obtained above (4 g) and 16% ammonia-methanol solution (100 ml) is allowed to stand at room temperature for 40 minutes. After evaporation of the solvent under reduced pressure, the residue is washed with diisopropyl ether to give (3R)-4-mercaptopyrrolidine-2-thione (4 g). The crude product thus obtained is used in the subsequent step without further purification.

Reference Example 5

(3S)-3-Acetylthiopyrrolidin-2-one is treated in the same manner as described in Reference Example 1-(2) to give (3S)-3-acetylthiopyrrolidine-2-thione.

M.p. 97–100° C.

$[\alpha]_D^{23}$ −126.6°(c =0.56, methanol)

Reference Example 6

A mixture of isopropoxycarbonyloxyethyl chloride (=2-chloroethyl isopropylcarbonate) (1.67 g), carbon tetrachloride (10 ml), sodium iodide (2.10 g) and anhydrous zinc chloride (0.08 g) is stirred at room temperature for 2 hours, and thereafter, ice water is added to the mixture. The organic layer is separated, and the aqueous layer is extracted twice with carbon tetrachloride. The combined organic layers are washed, dried and evaporated under reduced pressure to give isopropoxycarbonyloxyethyl iodide (=2-iodoethyl isopropylcarbonate) (1.48 g) as an oil.

NMR (CDCl$_3$) δppm: 1.31 (6H, d, J=6Hz), 2.20 (3H, d, J=6Hz), 5.00 (1H, m), 6.82 (1H, q, J=6Hz)

EFFECTS OF THE INVENTION

The compounds [I]of this invention which have a 2-thioxopyrrolidin-4-ylthio group at 2-position of 1-methyl-carbapenem nucleus and pharmaceutically acceptable salts thereof have excellent antimicrobial activities against a wide range of microorganisms including Gram positive and Gram negative bacteria, such as microorganisms of the genera Escherichia, Salmonella, Shigella, Klebsiella, Proteus, Morqanella, Providencia, Citrobacter, Bacteroides, Streptococcus, Staphylococcus, Enterobacter, Serratia, Pseudomonas, and the like, and further have high antimicrobial activities against clinically isolated pathogen:c strains, and hence, are useful for the treatment of infectious diseases by these microorganisms.

For example, the compounds of this invention have superior antimicrobial activity of 2 to 4 times higher against *Staphylococcus aureus, Staphylococcus epidermidis, Escherichia coli, Proteus vulgaris* and *Pseudomonas aeruginosa*, in comparison with the compounds having 2-oxopyrrolidin-4-ylthio group at 2-position as disclosed in Japanese Patent First Publication (Kokai) No. 49783/1990.

Besides, the compounds [I] and their pharmaceutically acceptable salts of this invention have advantageously higher stability against dehydropeptidase I owing to the introduction of 2-thioxopyrrolidin-4-ylthio group at 2-position of the 1-methylcarbapenem nucleus. For example, the compounds [I] of this invention have 2 times or more higher stability against dehydropeptidase I in comparison with the compounds disclosed in the above Japanese Patent First Publication No. 49783/1990.

Further, the compounds [I] and their pharmaceutically acceptable salts of this invention are characterized in that they are effective for treating inflammatory disease of biliary tract because of their high distribution into bile.

Furthermore, the compounds [I] and their pharmaceutically acceptable salts of this invention show high therapeutic effects because of their high absorbability by oral administration. For example, when orally administered to mice infected with *Staphylococcus aureus*, the compounds [I] of this invention show 2 to 8 times superior therapeutic effects in comparison with the compounds disclosed in Japanese Patent First Publication (Kokai) No. 49783/1990.

Moreover, the compounds [I] and their pharmaceutically acceptable salts of the invention have also lower toxicity and hence have higher safety. For example, when one of the compounds of this invention, (1R, 5S, 6S)-2-[(4R)-pyrrolidine-2-thion-4-ylthio]-6-[(1R)-1-hydroxyethl]-1-methylcarbapen-2-em-3-carboxylic acid isobutyryloxymethyl ester was orally administered to mice in a dose of 4,000 mg/kg, no death of the mice was observed even after 7 days.

Thus, the compounds [I] and their pharmaceutically acceptable salts of this invention are useful as an antimicrobial drug, for example, for the prophylaxis and treatment of various infectious diseases induced by various microorganisms as a chemotherapeutic drug for mammals including human being and also as an additive for animal feeds.

What is claimed is:

1. A mercaptan compound of the formula:

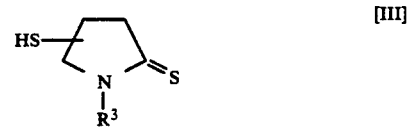

wherein $R^3$ is a hydrogen atom or a lower alkyl group, or a salt thereof.

2. The mercaptan compound claimed in claim 1, which has R configuration at the position of mercapto-substitution in the pyrrolidine ring.

3. The mercaptan coupond claimed in claim 1, which has S configuration at the position of mercapto-substitution in the pyrrolidine ring.

4. The mercaptan claimed in claim 2, which is the 4R-isomer.

5. Ther mercaptan compound claimed in claim 3, which is the 4S-isomer.

* * * * *